United States Patent [19]

Claeson et al.

[11] 4,242,329

[45] Dec. 30, 1980

[54] BRADYKININ-INHIBITING TRIPEPTIDE DERIVATIVES

[75] Inventors: Karl G. Claeson, Lidingö; Leif R. Simonsson, Hisings-Backa; Salo Arielly, Kungsbacka, all of Sweden

[73] Assignee: AB Kabi, Stockholm, Sweden

[21] Appl. No.: 58,333

[22] Filed: Jul. 17, 1979

[30] Foreign Application Priority Data

Jul. 18, 1978 [SE] Sweden ................................ 7807937

[51] Int. Cl.³ ...................... A61K 37/00; C07C 103/52
[52] U.S. Cl. .............................. 424/177; 260/112.5 R
[58] Field of Search ................... 424/177; 260/112.5 R

[56] References Cited

U.S. PATENT DOCUMENTS 4,110,322  8/1978  Greven et al. ............... 260/112.5 R Primary Examiner—Delbert R. Phillips
Attorney, Agent, or Firm—Pollock, Vande Sande & Priddy

[57] ABSTRACT

Tripeptide derivatives of the formula

H-D-X-Phe-Arg-Y in which

X is selected from the group consisting of Pro and Phe

Y is selected from the group consisting of O—$R_1$ and NH—$R_2$ in which $R_1$ is selected from the group consisting of straight, branched and cyclic alkyl group with 1-12 C atoms, and $R_2$ is selected from the group consisting of H, straight, branched and cyclic alkyl group with 1-12 C atoms, and physiologically acceptable salts thereof.

A process for producing said tripeptide derivatives by synthesis and purification methods which are known in the peptide chemistry.

Pharmaceutical preparations comprising said tripeptide derivatives.

24 Claims, No Drawings

BRADYKININ-INHIBITING TRIPEPTIDE DERIVATIVES

TECHNICAL FIELD

This invention is related to new bradykinin-inhibiting tripeptide derivatives, especially amides and esters.

The interaction of proteolytic enzymes, especially kallikrein, on the plasma protein kininogen, releases the nonapeptide:

Arg-Pro-Pro-Gly-Phe-Ser-Pro-Phe-Arg

Bradykinin (BK) exhibits strong pharmacodynamic activity. Also in extremely low doses BK causes vasodilation, bronchoconstriction, permeability increase in the capillary vessels, pain by influencing the nerve ends, contraction or relaxation of extravasal smooth muscles, e.g. in the intestines and uterus, accumulation leucocytes.

BACKGROUND ART

The mechanisms by which bradykinin is active, are only incompletely known, but probably there are several different receptors on the various target organs. Some of the effects of BK can probably also be mediated by the release of other active compounds, such as prostaglandines.

BK is probably involved in a number of different diseases, e.g. in inflammatory processes, shock by various causes, rheumatoid arthritis, gout, pancreatitis, carcinoid, migraine, hereditary angioneurotic oedema, burns, allergies.

It is probable that treatment with a suitable antagonist against BK would be advantageous for diseases in which the BK level is increased.

For many years scientists have searched for specific inhibitors of BK, however, without success in spite of the fact that a very large number of fragments and analogs of BK have been synthetized.

DISCLOSURE OF INVENTION

We have now surprisingly discovered that compounds of the following general formula:

H-D-X-Phe-Arg-Y in which X=Pro or Phe and Y=O—$R_1$ or NH—$R_2$ and in which $R_1$=a straight, branched or cyclic alkyl group with 1-12 C atoms and $R_2$=H, a straight, branched or cyclic alkyl group and physiologically acceptable salts thereof, give specific inhibition of bradykinin.

For the syntheses of the new BK antagonists conventional protective groups and coupling methods which are well-known in the peptide chemistry are used. The C terminal ester or amide groups are likewise coupled with synthesis methods which are well-known in the organic chemistry. The purification of the intermediate and final products is performed by precipitation, recrystallization or gel chromatographic separation.

The invention is illustrated by the following non-restricting examples.

ABBREVIATIONS

Amino acids (unless otherwise stated, L-configuration is intended)
Arg=arginine
Phe=phenyl alanine
Pro=proline
Others
AcOH=acetic acid
Boc=t-butyloxy carbonyl
Cbo=carbobenzoxy
DCCI=dicyclohexyl carbodiimide
DMF=dimethyl formamide
DMSO=dimethylsulphoxide
$Et_3N$=triethylamine
EtOAc=ethyl acetate
EtOH=ethanol
HBT=N-hydroxy benzotriazol
MeOH=methanol
OpNP=p-nitrophenoxy
i-PrOH=isopropyl alcohol
TFA=trifluoroacetic acid
TLC=thin layer chromatography

Thin layer chromatography

For the TLC analysis prepared ready-to-use glass sheets with silica gel $F_{254}$ (Merck) as absorbant are used. The following solvent systems are used (volume ratio):
A=n-butanol:AcOH:water (3:2:1)
$P_1$=chloroform:MeOH (9:1)
Pa=chloroform:MeOH:AcOH (17:2:2)
$Pa_6$=chloroform:MeOH:AcOH:$H_2O$ (34:4:9:2)
M=n-butanol: AcOH:$H_2O$:pyridine (30:6:24:20)

When the chromatography is finished the sheet is studied in UV light (254 nm) and is then developed with chlorine/-o-toluidine reagens according to the conventional method. The $R_f$ values stated are the result of separate chromatography treatments.

EXAMPLE I

H-D-Pro-Arg-O-heptyl·2HCl.
M.w. (molecular weight)=589.6

Ia. Cbo-Phe-Arg-($NO_2$)-OMe. M.w.=514.5.
27 g (0.10 moles) H-Arg ($NO_2$)-OMe·HCl dissolved in 4 ml DMF is neutralized when cooled with 18 ml $Et_3$NHCl formed is removed by filtration and thereafter 42 g (0.105 mole) Cbo-Phe-OpNP is added. The reaction is allowed to proceed with stirring for a night and the reaction mixture is then evaporated in vacuum to an oil which is dissolved in 500 ml EtOAc. The EtOAc phase is washed in sequence with 2% $NaHCO_3$ in $H_2O$, $H_2O$, HCl diluted with $H_2O$. After drying with $Na_2SO_4$ the EtOAc phase is evaporated to about 200 ml and precipitated by addition of ether. The crystalline precipitate is washed with ether and dried. It is according to the TLC pure.
Yield: 37.6 g (73%) of Ia
TLC: $R_f$=0.52 (P1).

Ib. Cbo-Phe-Arg($NO_2$)-OH. M.w.=500.5.
3.1 g (6.0 mmol) of Ia is dissolved in about 150 ml MeOH, and thereafter 7.3 mmol (7.3 ml/1 M NaOH in $H_2O$) is added. After about 4 hours the reaction mixture is evaporated in vacuum, dissolved in a small volume of $H_2O$ and washed twice with EtOAc. The $H_2O$ phase is acidified with HCl to pH=2, and thereafter formed Cbo-Phe-Arg($NO_2$)-OH is extracted with EtOAc (3 times). The EtOAc phase is washed with 10% NaCl in $H_2O$, dried with $Na_2SO_4$ and evaporated to dryness. The crystals formed are dried after leaching with ether. The product is pure according to TLC.
Yield: 2.86 g (95%) of Ib
TLC: $R_f$=0.14 (Pa).

Ic. Cbo-Phe-Arg($NO_2$)-O-heptyl. M.w.=598.7.

0.60 ml SOCl$_2$ (distilled) is added to 10 ml 1-heptanol under humidity-free conditions and with cooling in an ice bath. After stirring 1 hour at room temperature 1.00 g (2.0 mmol) of Ib is added. The reaction is finished after an hour and the reaction mixture is then a thick white mass. The reaction mixture is diluted with ether and the resulting heavy crystals are filtered off. The crystal mass is dissolved in MeOH and precipitated with H$_2$O (removes HCl formed). The obtained crystals are filtered off. TLC shows completely pure heptyl ester. Yield: 962 mg (80%) of Ic
TLC: R$_f$=0.60 (P1).

Id. Boc-D-Pro-Phe-Arg(NO$_2$)-O-heptyl. M.w.=661.8.

600 mg (1.0 mmol) of Ic is dissolved in 2 ml HOAc and 1.4 ml 5.6 M HBr in HOAc is added. The reaction mixture is then poured into about 100 ml dry ether. The precipitation formed is filtered off and washed with dry ether and dried in vacuum over NaOH. The obtained HBr salt of H-Phe-Arg(NO$_2$)-O-heptyl is dissolved in 2 ml DMF and neutralized at a low temperature (−10° C.) with Et$_3$N until basic reaction. The obtained Et$_3$N·Br is filtered off. To the reaction mixture is added 215 mg (1.0 mmol) of Boc-D-Pro-OH and 135 mg (1.0 mmol) of HBT and at a low temperature 250 mg (about 1.2 mmol) of DCCI. The reaction is allowed to continue over a night and resulting DCU is filtered off (after cooling) and the reaction mixture is evaporated in vacuum to an oil. The oil is kneeded with a small quantity of 2% NaHCO$_3$ in H$_2$O. The obtained mass is dissolved in a small amount of MeOH and chromatographed on a column with Sephadex LH-20 in MeOH with MeOH as an eluant. The fraction comprising pure Id is dissolved with H$_2$O and MeOH is evaporated in vacuum. Id is precipitated as a heavy powder which is recovered and dried in vacuum.
Yield: 570 mg (86%) of Id
TLC: R$_f$=0.65 (Pa), 0.52 (P1).

I. H-D-Pro-Phe-Arg-O-hepthyl·2HCl. M.w.=589.6.

400 mg (0.6 mmol) of Id is deprotected with 30 ml HF at 0° C. for an hour in the presence of 0.4 ml anisol. After evaporation in vacuum the product is dissolved in 20 ml of 2% HOAc in H$_2$O and washed several times with a small quantity of ether. The H$_2$O phase is chromatographed on a column with SephadexG-15 in 2% HOAc with the same medium for elution. The fraction containing the slightly contaminated acetate of I is freeze-dried and ion exchanged on a column with QAE-25 (Pharmacia Fine Chemicals) in chloride form in 50% EtOH-50% H$_2$O with the same medium for eluation. A fraction with completely pure I is obtained.
Yield: 318 mg (89%) of I
TLC: R$_f$=0.27 (A) only shows one spot.
Amino acid analysis: Arg 1.00, Phe 1.02, Pro 0.99.

EXAMPLE II

H-D-Pro-Phe-Arg-NH-heptyl·2HCl. M.w.=588.6.

IIa. Cbo-Phe-Arg(NO$_2$)-NH-heptyl. M.w.=597.7.

1.0 g (2.0 mmol) of Cbo-Phe-Arg(NO$_2$)-OH (Ib) and 0.27 mg (2.0 mmol) of HBT is dissolved in 5.0 ml DMF, and thereafter 0.50 g (about 2.4 mmol) DCCI is added with cooling on an ice bath. After about 1 hour 0.33 ml (2.2 mmol) heptylamine is added. The reaction is allowed to proceed with stirring over a night, and thereafter formed DCU is filtered off and the reaction mixture evaporated in vacuum to an oil. The oil is kneeded with H$_2$O, 2% NaHCO$_3$, H$_2$O, 2% KHSO$_4$, H$_2$O and finally with pure H$_2$O. The obtained mass is crystallized from MeOH=H$_2$O. TLC shows a minor by-product R$_f$=0.54 (Pa) together with the main product R$_f$=0.58 (Pa).
Yield: 1.13 g (94%) of IIa.

IIb. Boc-D-Pro-Phe-Arg-NO$_2$-NH-heptyl. M.w.=660.8.

1.0 g (1.67 mmol) of IIa is deprotected with 4 ml HOAc and 2.8 ml HBr in the same way as Ic in Example I. TLC of the HBr salt of H-Phe-Arg(NO$_2$)-NH-heptyl is contaminated with a minor amount of a by-product R$_f$=0.72 (Pa$_6$) together with the main product R$_f$=0.61 (Pa$_6$). The HBr salt is ion exchanged on a column with QAE-25 in chloride form in 90% EtOH-10% H$_2$O with the same medium for eluation. A fraction with the pure main product in chloride form is obtained, 496 mg (1.0 mmol), which is dissolved in 2 ml DMF and neutralized with 0.15 ml Et$_3$N. Thereafter 215 mg (1.0 mmol) Boc-D-Pro-OH, 135 mg (1.0 mmol) HBT and under cool conditions 250 mg (about 1.2 mmol) DCCI are added. The reaction is finishes after 20 hours, and thereafter the reaction mixture is filtered and evaporated in vacuum to an oil which is kneeded with 2% NaHCO$_3$ in H$_2$O and pure H$_2$O. The obtained mass is dissolved in MeOH and chromatographed on a column with Sephadex LH-20 in MeOH with MeOH as eluating agent. The fraction with pure IIb is evaporated in vacuum och leached with H$_2$O. The obtained crystal mass is dried in vacuum.
Yield: 457 mg (69%) of IIb
TLC: R$_f$=0.35 (P1). II. H-D-Pro-Phe-Arg-NH-heptyl·2HCl. M.w.=588.6.

300 mg of IIb is deprotected in the same way as Id in Example I. Further purification is performed in the same way as in Example I.
Yield: 263 mg (98%) of II
TLC: R$_f$=0.25 (A) shows only one spot.
Amino acid analysis: Arg 1.00, Phe 0.97, Pro 0.98.

EXAMPLE III

H-D-Pro-Phe-Arg-NH$_2$·2HCl. M.w.=490.5.

IIIa. Boc-D-Pro-Phe-OMe. M.w.=376.4.

4.2 g (19.5 mmol) Boc-D-Pro-OH and 2.7 g (20.0 mmol) HBT are dissolved in 50 ml DMSO. 4.4 g (about 21 mmol) DCCI is added with stirring and under cool conditions. A solution of 4.3 g (20.0 mmol) H-Phe-OMe-HCl in 50 ml DMF which is previously neutralized under cool conditions with 2.8 ml (20.0 mmol) Et$_3$N and thereafter filtered, is added to the reaction mixture. The reaction is allowed to proceed over a night, and thereafter formed DCU is filtered off. The reaction mixture is evaporated in vacuum to an oil which is dissolved in 300 ml EtOAc. The EtOAc solution is washed in sequence with 2% NaHCO$_3$ in H$_2$O, H$_2$O, 2% KHSO$_4$ in H$_2$O and finally H$_2$O, and is then dried with Na$_2$SO$_4$. The EtOAc solution is evaporated in vacuum to dryness and the obtained crystal mass is treated with petroleum ether, filtered and washed with petroleum ether. The crystal mass is dried in vacuum.
Yield: 5.5 g (75%) of IIIa
TLC: R$_f$=0.53 (P1).

IIIb. Boc-D-Pro-Phe-OH. M.w.=362.4

4.5 g (12.0 mmol) of IIIa is dissolved in 50 ml MeOH and 15 ml 1 N NaOH (15 mmol) is added. After 2 to 3 hours with stirring at room temperature evaporation to dryness is performed. The obtained mass is dissolved in 100 ml H$_2$O and washed twice with 50 ml ether, and thereafter the aqueous phase is acidified with KHSO$_4$ to pH=3. After stirring at 0° C. for 30 minutes the formed precipitate is filtered and washed with a small amount of cold water. The precipitate is then dried in vacuum.
Yield: 3.2 g (74%) of IIIb
TLC: $R_f$=0.81 (Pa$_6$).

IIIc. Boc-D-Pro-Phe-Arg(NO$_2$)-NH$_2$. M.w.-562.6.

0.65 g (1.8 mmol) of IIIb and 0.26 g (1.9 mmol) HBT are dissolved in 10 ml DMF. 0.38 g (about 1.8 mmol) DCCI is added with stirring and under cool conditions. To the reaction mixture is added a solution of 0.6 g (2 mmol) H-Arg(NO$_2$)-NH$_2$·HBr in 10 ml DMF (must be heated and cooled again before neutralization) which is first neutralized under cool conditions with 0.3 ml (2.2 mmol) Et$_3$N and thereafter filtered. The reaction is allowed to proceed over a night, and therafter formed DCU is filtered off. The reaction mixture is evaporated in vacuum to an oil which is dissolved in boiling EtOAc (100 ml). A precipitate is obtained on cooling and is washed with EtOAc and ether. The precipitate (about 0.5 g) is dissolved in a larger quantity of EtOAc and washed in sequence with 2% NaHCO$_3$, H$_2$O, H$_2$O, 2% KHSO$_4$ and finally H$_2$O. The EtOAc solution is dried with Na$_2$SO$_4$ and thereafter evaporated in vacuum to dryness.
Yield: 480 mg (48%) of IIIc
TLC: $R_f$=0.73 (Pa$_6$).

III. H-D-Pro-Phe-Arg-NH$_2$·2HCl. M.w.=490.5.

160 mg (0.28 mmol) of IIIc is deprotected with about 10 ml of HF at 0° C. for 50 minutes in the presence of 0.3 ml of anisol. After evaporation in vacuum the substance is dissolved in about 6 ml of 50% EtOH-50% H$_2$O and is ion exchanged on a column containing QAE-25 in the chloride form in 50% EtOH-50% H$_2$O with the same medium for eluation. The fraction with III is evaporated in vacuum, dissolved in about 5 ml of MeOH and chromatographed on a column with Sephadex LH-20 in MeOH with MeOH as medium for eluation. The fraction with pure III is freeze-dried.
Yield: 100 mg (71%) of III
TLC: $R_f$=0.34 (M) shows only one spot.
Amino acid analysis: Arg 1.00, Phe 1.01, Pro 0.98.

EXAMPLE IV

H-D-Pro-Phe-Arg-O-i-Pr·2HCl. M.w.=533.5.

IVa. H-Arg(NO$_2$)-O-i-Pr·HCl. M.w.=297.8.

5.5 g (25 mmol) of Arg(NO$_2$) is dissolved in 250 ml of isopropanol and thereafter esterification is achieved with repeated treatments with dry HCl gas in the usual manner. When the reaction is judged to be finished the reaction mixture is evaporated to dryness in vacuum. The ester (IVa) is obtained by crystallizing by dissolving the evaporated mass in a small quantity of hot isopropanol and thereafter precipitating with dry ether when the solvent has been cooled off. The recovered crystals are washed 3 times with dry ether.
Yield: 5.8 g (78%) of IVa
Melting point: 179°–181° C.

IVb. Boc-D-Pro-Phe-Arg(NO$_2$)-O-i-Pr. M.w.=605.7.

Procedure, reagents and quantities are the same as according to Example IIIc but 0.60 g (2.0 mmol) of IVa is used instead of H-Arg(NO$_2$)-NH$_2$·HBr.
Yield: 440 mg (40%) of IVb
TLC: $R_f$=0.41 (Pl).

IV. H-D-Pro-Phe-Arg-O-i-Pr. M.w.=533.5.

300 mg (0.50 mmol) of IVb is deprotected with HF in the presence of anisol in the same way as in Example I. The product is purified and ion exchanged in the same way as in Example I.
Yield: 180 mg (68%) of IV
TLC: $R_f$=0.21 (A) shows only one spot.
Amino acid analysis: Arg 1.00, Phe 1.00, Pro 0.98.

EXAMPLE V

H-D-Phe-Phe-Arg-NH$_2$·2HCl. M.w.=540.5.

Va. Cbo-D-Phe-Phe-OMe. M.w.=460.5.

Procedure, reagents and quantities are as in Example IIIa but with 6.0 g (20 mmol) of Cbo-D-Phe-OH instead of Boc-D-Pro-OH.
Yield: 6.2 g (67%) of Va
TLC: $R_f$=0.60 (Pl).

Vb. Cbo-D-Phe-Phe-OH. M.w.=446.5.

6.0 g (13.0 mmol) of Va is hydrolyzed with NaOH in exactly the same way as in Example IIIb.
Yield: 4.9 g (84%) of Vb
TLC: $R_f$=0.85 (Pa$_6$).

Vc. Cbo-D-Phe-Phe-Arg(NO$_2$)-NH$_2$·M.w.=646.7.

Procedure, reagents and quantities are as in Example IIIc but with 0.89 g (2.0 mmol) of Vb instead of IIIb.
Yield: 505 mg (39%) of Vc
TLC: $R_f$=0.80 (Pa$_6$).

V. H-D-Phe-Phe-Arg-NH$_2$·2HCl. M.w.=540.5.

400 mg (0.62 mmol) of Vc is deprotected, purified and ion exchanged in the same way as in Example I.
Yield: 296 g (88%) of I
TLC: $R_f$=0.37 (M) shows only one spot.
Amino acid analysis: Arg 1.00, Phe 1.97.

EXAMPLE VI

H-D-Phe-Phe-Arg-NH-heptyl·2HCl. M.w.=638.7.

VIa. Cbo-D-Phe-Phe-Arg(NO$_2$)-NH-heptyl. M.w.=744.9.

Procedure, reagents and quantities are as in Example IIb but with Cbo-D-Phe-OH instead of Boc-D-Pro-OH.
Yield: 470 mg (63%) of VIa
TLC: $R_f$=0.42 (Pl).

VI. H-D-Phe-Phe-Arg-NH-heptyl·2HCl, M.w.=638.7.

300 mg (0.40 mmol) of VIa is deprotected, purified and ion exchanged in the same way as in Example I.
Yield: 176 mg (59%) of VI
TLC: $R_f$=0.28 (A) shows only one spot.
Amino acid analysis: Arg 1.00, Phe 1.98.

EXAMPLE VII

H-D-Pro-Phe-Arg-NH-lauryl·2HCl. M.w.=658.7.

VIIa. Cbo-Phe-Arg(NO$_2$)-NH-lauryl. M.w.=667.8.

Procedure, reagents and quantities are as in Example IIa but with 0.41 g (2.2 mmol) of laurylamine as amine instead of heptylamine.
Yield: 1.17 g (88%) of VIIa
TLC: $R_f$=0.60 (Pa) is homogeneous.

VIIb. Boc-D-Pro-Phe-Arg(NO$_2$)-NH-lauryl. M.w.=730.9.

Procedure, reagents and quantities are as in Example IIb but with 0.67 g (1.0 mmol) of VIIa as starting peptide instead of 1.67 mmol of IIa in Example IIb. Furthermore, the HBr salt of H-Phe-Arg(NO$_2$)-NH-lauryl can be used without further purification on the ion exchanger.
Yield: 585 mg (80%) of VIIb.
TLC: $R_f$=0.39 (Pl).

VII.    H-D-Pro-Phe-Arg-NH-lauryl·2HCl.
M.w.=658.7.

300 mg (0.41 mmol) of VIIb is deprotected, purified and ion exchanged in the same way as in Example I.
Yield: 230 mg (85%) of VII.
TLC: $R_f=0.27$ (A) shows only one spot.
Amino acid analysis: Arg 1.00, Phe 0.98, Pro 0.99.

EXAMPLE VIII

H-D-Phe-Phe-Arg-NH-i-Pr·2HCl. M.w.=582.6.

VIIIa. Cbo-Phe-Arg(NO$_2$)-NH-i-Pr. M.w.=541.6.
Procedure, reagents and quantities are the same as in Example IIa but with 130 mg (2.2 mmol) of isopropylamine as amine instead of heptylamine.
Yield: 0.95 g (88%) of VIIIa.
TLC: $R_f=0.51$ (Pa) shows one spot.
VIIIb.    Cbo-D-Phe-Phe-Arg(NO$_2$)-NH-i-Pr.
M.w.=688.8.

Procedure, reagents and quantities are the same as in Example VIa but with 0.54 g (1.0 mmol) of VIIIa as protected dipeptide instead of IIa.
Yield: 470 mg (68%) of VIIIb
TLC: $R_f=0.38$ (Pl).
VIII.    H-D-Phe-Phe-Arg-NH-i-Pr·2HCl.
M.w.=582.6.

300 mg (0.44 mmol) of VIIIb is deprotected, purified and ion exchanged in the same way as in Example I.
Yield: 205 mg (80%) of VIII
TLC: $R_f=0.23$ (A) shows only one spot.
Amino acid analysis: Arg 1.00, Phe 1.97.

EXAMPLE IX

H-D-Phe-Phe-Arg-NH-cyclohexyl·2HCl.
M.w.=622.7.

IXa.    Cbo-Phe-Arg(NO$_2$)-NH-cyclohexyl.
M.w.=581.7.

Procedure, reagents and quantities are the same as in Example IIa but with 218 mg (2.2 mmol) of cyclohexylamine as amine instead of heptylamine.
Yield: 0.90 g (77) of IXa
TLC: $R_f=0.60$ (Pa) shows one spot.
IXb.    Cbo-D-Phe-Phe-Arg(NO$_2$)-NH-cyclohexyl.
M.w.=728.8.

Procedure, reagents and quantities are the same as in Example VIa but with 0.58 g (1.0 mmol) of IXa as protected dipeptide instead of IIa.
Yield: 520 mg (71%) of IXb
TLC: $R_f=0.49$ (Pl).
IX.    H-D-Phe-Phe-Arg-NH-cyclohexyl·2HCl.
M.w.=622.7.

300 mg (0.41 mmol) of IXb is deprotected, purified and ion exchanged in the same way as in Example I.
Yield: 185 mg (72%) of IX
TLC: $R_f=0.28$ (A).
Amino acid analysis: Arg 1.00, Phe 1.96.

The bradykinin-inhibiting activity of the new tripeptide derivatives is evident from the following disclosure of the biological evaluation on isolated organs. The bradykinin-inhibiting activity is studied on isolated rat uterus. The rats are pretreated subcutaneous with 0.2 mg/kg of diethyl stilbestrol, 12–15 hours prior to the experiment. The muscle from uterus which is longitudinally sectioned into halves is arranged in a smooth muscle bath with de Jalon's buffer (de Jalon et al., Farmacother.Acta, Vol. 3, p. 313, 1945), oxygenated with carbogene gas (5% carbon dioxide, 95% oxygen). The temperature is maintained at 35° C. The muscle is stretched with a tension corresponding to 0.5 g. The isometric tension is measured with Grass (FT 03C) force transmitter connected to a Grass polygraph.

Muscle contractions for bradykinin in bath concentrations of $10^{-11} - 10^{-6}$ M (mole/liter) are registrated, and thereafter the concentration of bradykinin which induces 70% of maximum muscle contraction (ED$_{70}$) is evaluated. The bradykinin inhibiting activity is then tested with the tripeptide derivatives in bath concentrations of $10^{-8}$, $10^{-7}$, $10^{-6}$ and $10^{-5}$ M, against the ED$_{70}$ for bradykinin of resp. muscle. For each concentration the tripeptide derivatives are incubated with the uterus tissue 5 and 10 minutes resp. before the addition of bradykinin. The bradykinin-inhibiting activity is expressed as the time in minutes required until bradykinin again gives the original contraction. Each addition of bradykinin is followed by washing with the buffer.

TABLE

| Bradykinin inhibiting tripeptide derivative | According to Example No. | Conc. in test bath, mole/liter | Inhibition of bradykinin effect, % | Duration of inhibition, minutes |
|---|---|---|---|---|
| H-D-Pro-Phe-Arg-O-heptyl | I | $10^{-8}$ | 10 | 15 |
|  |  | $10^{-7}$ | 10 | 15 |
|  |  | $10^{-6}$ | 100 | 15 |
|  |  | $10^{-5}$ | 100 | 35 |
| H-D-Pro-Phe-Arg-NH-heptyl | II | $10^{-8}$ | 15 | 15 |
|  |  | $10^{-7}$ | 15 | 20 |
|  |  | $10^{-6}$ | 100 | 30 |
|  |  | $10^{-5}$ | 100 | 45 |
| H-D-Pro-Phe-Arg-NH$_2$ | III | $10^{-8}$ | 15 | 15 |
|  |  | $10^{-7}$ | 15 | 15 |
|  |  | $10^{-6}$ | 100 | 30 |
|  |  | $10^{-5}$ | 100 | 50 |

We claim:
1. Tripeptide derivatives of the formula

H-D-X-Phe-Arg-Y in which
X is selected from the group consisting of Pro and Phe
Y is selected from the group consisting of O—R$_1$ and NH—R$_2$ in which
R$_1$ is selected from the group consisting of straight, branched and cyclic alkyl group with 1–12 C atoms, and
R$_2$ is selected from the group consisting of H, straight, branched and cyclic alkyl group with 1–12 C atoms, and physiologically acceptable salts thereof.

2. The tripeptide derivative of claim 1 wherein X is Pro.

3. The tripeptide derivative of claim 4 wherein Y is O—R.

4. The tripeptide derivative of claim 1 wherein Y is O—R.

5. The tripeptide derivative of claim 1 wherein Y is O-heptyl.

6. The tripeptide derivative of claim 2 wherein Y is $NHR_2$.

7. The tripeptide derivative of claim 1 wherein Y is $NHR_2$.

8. The tripeptide derivative of claim 1 wherein Y is NH heptyl.

9. The tripeptide derivative of claim 1 wherein Y is $NH_2$.

10. The tripeptide derivative of claim 1 wherein Y is O-isopropyl.

11. The tripeptide derivative of claim 1 wherein X is Phe.

12. The tripeptide derivative of claim 1 wherein Y is NH lauryl.

13. The tripeptide derivative of claim 1 wherein Y is NH cyclohexyl.

14. The tripeptide derivative of claim 1 wherein X is Pro and Y is O-heptyl.

15. The tripeptide derivative of claim 1 wherein X is Pro and Y is NH-heptyl.

16. The tripeptide derivative of claim 1 wherein X is Pro and Y is $NH_2$.

17. The tripeptide derivative of claim 1 wherein X is Pro and Y is O-isopropyl.

18. The tripeptide derivative of claim 1 wherein X is Phe and Y is $NH_2$.

19. The tripeptide derivative of claim 1 wherein X is Phe and Y is NH heptyl.

20. The tripeptide derivative of claim 1 wherein X is Pro and Y is NH lauryl.

21. The tripeptide derivative of claim 1 wherein X is Phe and Y is NH isopropyl.

22. The tripeptide derivative of claim 1 wherein X is Phe and Y is NH cyclohexyl.

23. Pharmaceutical preparation for the inhibition of bradykinin which comprises the tripeptide derivative of claim 1 in an amount sufficient to inhibit the formation of bradykinin.

24. A process for inhibiting the formation of bradykinin which comprises administering to a host the pharmaceutical preparation of claim 23.

* * * * *